United States Patent [19]

Nonn

[11] Patent Number: 4,990,705

[45] Date of Patent: Feb. 5, 1991

[54] PREPARATION OF 4-BROMOBIPHENYL

[75] Inventor: Alain Nonn, Sainte Foy Les Lyon, France

[73] Assignee: Rhone-Poulenc Chimie, Courbevoie, France

[21] Appl. No.: 341,812

[22] Filed: Apr. 24, 1989

[30] Foreign Application Priority Data

Apr. 22, 1988 [FR] France ................... 88 05331

[51] Int. Cl.$^5$ ....................... C07C 17/12; C07C 25/18
[52] U.S. Cl. ..................... 570/206; 570/208
[58] Field of Search ................. 570/206, 208, 210

[56] References Cited

U.S. PATENT DOCUMENTS 1,835,754  12/1931  Britton et al. ............... 570/206
3,622,640  11/1971  Taylor et al. ............... 570/206
3,636,170  1/1972   Notaro et al. ............... 570/206

FOREIGN PATENT DOCUMENTS 62-12728  1/1987  Japan ...................... 570/206
981833    1/1965  United Kingdom ............ 570/206

OTHER PUBLICATIONS

Schubert et al., *Jacs*, 91, 1443–1451 (1969).
Varma et al., *Ind. Chem. Soc. Quarterly*, vol. 4, (1927).

*Primary Examiner*—Werren B. Lone
*Attorney, Agent, or Firm*—Burns, Doane, Swecker & Mathis

[57] ABSTRACT

4-Bromobiphenyl is selectively produced in high yields, and in high conversions, by monobrominating biphenyl in a solvent reaction medium containing at least one organosulfur compound, amide, nitrile or acid having a pKa of at least 3.

18 Claims, No Drawings

PREPARATION OF 4-BROMOBIPHENYL

CROSS-REFERENCE TO COMPANION APPLICATION

My copending application, Ser. No. 341,818 filed Apr. 24, 1989 filed concurrently herewith and assigned to the assignee hereof.

BACKGROUND OF THE INVENTION

1. Field of the Invention

The present invention relates to the preparation of 4-bromobiphenyl, a known compound useful for a wide variety of applications, e.g., as an intermediate in the production of agrochemical and pharmaceutical compounds, as well as for the production of liquid crystals.

2. Description of the Prior Art

4-Bromobiphenyl is typically prepared by a monobromination of biphenyl A problem in such synthesis is to avoid the formation of dibromobiphenyl as much as possible, while at the same time maintaining a high conversion ratio of the biphenyl.

SUMMARY OF THE INVENTION

Accordingly, a major object of the present invention is the provision of an improved process for the monobromination of biphenyl, which improved process minimizes the byproduction of dibromobiphenyl and is well adopted for application on an industrial scale.

Briefly, the present invention features the preparation of 4-bromobiphenyl by reacting biphenyl with bromine in a reaction medium containing a solvent selected from among one organosulfur compound, an amide, a nitrile and an acid having a pKa of at least 3.

DETAILED DESCRIPTION OF THE PREFERRED EMBODIMENTS OF THE INVENTION

More particularly according to the present invention, the subject process permits the attainment, at ambient temperature, of yields of 4-bromobiphenyl higher than at least 65% and, in certain cases, at least 75%.

The critical characteristic of the process of the invention entails conducting the monobromination reaction in a reaction medium containing a particular solvent that must be inert relative to the bromine.

An especially preferred solvent comprises an organosulfur compound.

Examples of such organosulfur compounds are dimethylsulfoxide, the sulfolanes, and the like.

Another class of solvents that may be used in the process of the invention is that of the amides.

In particular, N,N-dimethylformamide (DMF), N,N-dimethylacetamide, N-methylacetamide, derivatives of piperidine, such as 1-formylpiperidine, N-methylpyrrolidone, and the like, are representative.

The solvent may also be selected from among the nitriles. Exemplary thereof are acetonitrile, n-butyronitrile, lactonitrile, and the like.

A final class of solvents comprises acids having a pKa greater than 3.

In a preferred embodiment of the invention, acids having a pKa of at least 4 are used.

Such acids are preferably carboxylic acids.

Thus, acetic acid, propionic acid, etc., are exemplary.

Of course, conducting the reaction in a reaction medium containing a mixture of the aforementioned solvents is also within the scope of this invention.

It should be appreciated that the process of the invention may be carried out in a reaction medium based on a mixture of water and at least one of the above solvents In such a case, a clear improvement in the kinetics of the reaction is noted.

In another preferred embodiment of the invention, the reaction medium contains at least one acid, in particular a carboxylic acid of the type described above, but the reaction is, furthermore, conducted in the presence of a catalytic system based on a component selected from among the Lewis acids and iodine.

Exemplary Lewis acids, preferably, are those containing an element belonging to Groups IIb, IIIa, IVb, Va, Vb, VIa and VIII of the Periodic Table. Representative are iron, zinc, antimony, tellurium, zirconium, titanium, aluminum, gallium, hafnium, niobium, phosphorus and boron.

The halides of these elements are especially preferred, such as, for example, $FeCl_3$, $ZnCl_2$, $SbCl_5$, $PBr_3$, $AlCl_3$; $TiCl_4$ and $ZrCl_4$.

In general, the catalytic system contains a single component of the type described above. However, it is possible to use a base system of at least two components.

Typically, the amount of the catalyst ranges from 0.1% to 10%, expressed in moles relative to the biphenyl employed, and more preferably ranges from 0.5% to 2%.

In another preferred embodiment of the invention, it is possible to carry out the bromination in a reaction medium containing, in addition to the acid having a pKa of at least 3 of a type described above, an acid having a pKa of less than 3.

For the latter type of acid, particularly representative are the carboxylic or sulfonic acids. More particularly, such acids substituted with at least one or more halogen atom substituents, notably fluorine, are used.

Exemplary thereof are trifluoroacetic acid, trifluoromethylsulfonic, etc.

In this embodiment, it should be appreciated that the proportion by volume of the acid having a pKa less than 3 preferably constitutes at most 50% of the total mixture of the acid having a pKa of at least 3 with the acid having a pKa less than 3.

The reaction is typically carried out by pouring the bromine into a mixture containing the biphenyl, the solvent and the catalyst system.

Usually, the bromine is employed in a stoichiometric excess of from 0% to 120%, more particularly an at least 50% stoichiometric excess, especially in the case of a catalytic system containing at least two of the aforesaid components.

It has now been confirmed that in spite of an excess of bromine, and even employing lengthy reaction times (these may range from approximately 10 to 30 hours), there is no appreciable formation of the dibromide derivative.

The reaction is advantageously carried out at a temperature of from 0° to 60° C., but preferably is carried out at ambient temperature.

Lastly, the desired 4-bromobiphenyl final product may be separated from the reaction medium by any known means, in particular by crystallization.

In order to further illustrate the present invention and the advantages thereof, the following specific examples are given, it being understood that same are intended only as illustrative and in nowise limitative.

EXAMPLE 1

Into a 250 ml reactor equipped with magnetic agitation means, a condenser, a dropping funnel, and a thermometer, the following materials were introduced:

(i) 15.4 g biphenyl (0.1 M);
(ii) 100 ml solvent at ambient temperature Then, over 10 min, the bromine was poured therein (39.2 g/0.22 M), whereupon the mixture was agitated for a varying period of time at ambient temperature. Upon completion of the reaction, the excess bromine was consumed by sodium or potassium sulfite or bisulfite. The organic phase was washed, dried and diluted to a given volume, and analyzed by CPG.

The results are reported in Table I.

EXAMPLE 2

The process was carried out as in Example 1, but with acetic acid as the solvent and using a catalytic system. The results are reported in Table II.

EXAMPLE 3

The following materials were introduced into the apparatus of Example 1:

(i) 7.72 g (0.05 mole) biphenyl;
(ii) 45 ml acetic acid; and
(iii) 5 ml trifluoroacetic acid.

Over 18 min, at ambient temperature, 17.6 g (0.11 mole) bromine were poured into the reaction vessel.

The operation was carried out as in the preceding examples. The results were as follows:

|  | Yield |
| --- | --- |
| Reaction time | 8 h |
| 2-Bromobiphenyl | 3.0% |
| 4-Bromobiphenyl | 78.1% |
| 4,4'-Dibromobiphenyl | 17.0%. |

TABLE I

| Experiment | Solvent | Duration (H) | Yield % | | | |
| --- | --- | --- | --- | --- | --- | --- |
|  |  |  | 2-Br | 4-Br | 2,4'-diBr | 4,4'-diBr |
| 1 | AcOH | 29 | 4.4 | 74.0 | 1.0 | 17.0 |
| 2 | AcOH 30 H2O 70 | 8 | 3.1 | 68.8 | 1.2 | 29.1 |
| 3 | CS2 | 21 | 5.9 | 86.5 | 0 | 4.9 |
| 4 | DMF | 21 | 7.8 | 77.9 | 1.3 | 15.9 |
| 5 | CH3CN | 24 | 3.1 | 66.0 | 1.1 | 27.8 |

TABLE II

| Experiment | Solvent | Catalyst | Duration (H) | Yield % | | | |
| --- | --- | --- | --- | --- | --- | --- | --- |
|  |  |  |  | 2-Br | 4-Br | 2,4'-diBr | 4,4'-diBr |
| 6 | AcOH | I2 (1%) | 28 h | 4.4 | 75.5 | 1.0 | 14.4 |
| 7 | AcOH | ZnCl2 (1%) | 25 h | 5.1 | 85.5 | 1.1 | 15.8 |
| 8 | AcOH | FeCl3 (1%) | 7 h | 4.4 | 79.5 | 0 | 13.7 |

While the invention has been described in terms of various preferred embodiments, the skilled artisan will appreciate that various modifications, substitutions, omissions, and changes may be made without departing from the spirit thereof Accordingly, it is intended that the scope of the present invention be limited solely by the scope of the following claims, including equivalents thereof.

What is claimed is:

1. A process for the preparation of 4-bromobiphenyl, comprising reacting biphenyl with bromine in a solvent reaction medium which comprises at least one organosulfur compound, amide or nitrile, which is inert relative to the bromine.

2. The process as defined by claim 1, said solvent reaction medium further comprising water.

3. The process as defined by claim 1, said solvent reaction medium comprising an organosulfur compound.

4. The process as defined by claim 1, said solvent reaction medium comprising an amide.

5. The process as defined by claim 1, said solvent reaction medium comprising a nitrile.

6. The process as defined by claim 1, said solvent reaction medium comprising an acid having a pKa of at least 3.

7. The process as defined by claim 6, said acid having a pKa of at least 4.

8. The process as defined by claim 6, said acid comprising a carboxylic acid.

9. The process as defined by claim 6, said solvent reaction medium further comprising a catalytic system based on a Lewis acid or iodine.

10. The process as defined by claim 9, said catalytic system comprising a Lewis acid containing an element of Groups IIb, IIIa, IVb, Va, Vb, VIa or VIII of the Periodic Table.

11. The process as defined by claim 10, said catalytic system comprising a Lewis acid halide.

12. The process as defined by claim 1, carried out using an at least 50% stoichiometric excess of bromine.

13. The process as defined by claim 6, said solvent reaction medium further comprising an acid having a pKa of less than 3.

14. The process as defined by claim 13, wherein the volume of acid having a pKa of less than 3 is no more than 50% of the total volume of acids.

15. The process as defined by claim 3, said organosulfur compound comprising carbon disulfide, dimethylsulfoxide, or a sulfolane.

16. The process as defined by claim 4, said amide comprising N-N-dimethylformamide, N,N-dimethylacetamide, N-methylacetamide, 1-formylpiperidine or N-methylpyrrolidone.

17. The process as defined by claim 5, said nitrile comprising acetonitrile, n-butyronitrile or lactonitrile.

18. A process for the preparation of 4-bromobiphenyl, comprising reacting biphenyl with bromine in a solvent reaction medium which comprises at least one organosulfur compound, amide, nitrile, or acid having a pKa of at least 3, which is inert relative to the bromine, resulting in products consisting of brominated biphenyls.

* * * * *